United States Patent
Constantz

(12) 
(10) Patent No.: US 6,719,993 B2
(45) Date of Patent: *Apr. 13, 2004

(54) CALCIUM PHOSPHATE CEMENTS PREPARED FROM SILICATE SOLUTIONS

(75) Inventor: Brent R. Constantz, Menlo Park, CA (US)

(73) Assignee: Skeletal Kinetics, LLC, Cupertino, CA (US)

( * ) Notice: Subject to any disclaimer, the term of this patent is extended or adjusted under 35 U.S.C. 154(b) by 118 days.

This patent is subject to a terminal disclaimer.

(21) Appl. No.: 10/109,994

(22) Filed: Mar. 29, 2002

(65) Prior Publication Data

US 2002/0098245 A1 Jul. 25, 2002

Related U.S. Application Data

(63) Continuation-in-part of application No. 09/561,324, filed on Apr. 28, 2000, now Pat. No. 6,375,935.

(51) Int. Cl.[7] .................................................. A61F 2/00
(52) U.S. Cl. ....................... 424/423; 424/400; 424/401; 424/422; 424/426; 424/484; 424/489; 514/951; 514/953
(58) Field of Search ................................. 424/400, 401, 424/489, 422, 423, 57, 426, 484, 49; 514/951, 953

(56) References Cited

U.S. PATENT DOCUMENTS

| | | | |
|---|---|---|---|
| 4,160,012 A | 7/1979 | Ono et al. | |
| 4,161,511 A | 7/1979 | Shiraki et al. | |
| 4,165,368 A | * 8/1979 | Gaffar | 424/52 |
| 4,429,691 A | 2/1984 | Niwa et al. | |
| 4,497,075 A | 2/1985 | Niwa et al. | |
| 4,735,857 A | 4/1988 | Tagai et al. | |
| 4,990,163 A | 2/1991 | Ducheyne et al. | |
| 5,049,157 A | 9/1991 | Mittelmeier et al. | |
| 5,218,035 A | 6/1993 | Liu | |
| 5,266,534 A | 11/1993 | Atsumi et al. | |
| 5,281,265 A | 1/1994 | Liu | |
| 5,427,768 A | 6/1995 | Tung | |
| 5,460,803 A | 10/1995 | Tung | |
| 5,525,148 A | 6/1996 | Chow et al. | |
| 5,534,244 A | 7/1996 | Tung | |
| 5,545,254 A | 8/1996 | Chow et al. | |
| 5,580,623 A | 12/1996 | Fulmer et al. | |
| 5,605,713 A | 2/1997 | Boltong | |
| 5,626,861 A | 5/1997 | Laurencin et al. | |
| 5,648,097 A | 7/1997 | Nuwayser | |
| 5,660,624 A | 8/1997 | Dry | |
| 5,665,121 A | 9/1997 | Gie et al. | |
| 5,679,294 A | 10/1997 | Umezu et al. | |
| 5,681,872 A | 10/1997 | Erbe | |
| 5,691,397 A | 11/1997 | Glimcher et al. | |
| 5,695,729 A | 12/1997 | Chow et al. | |
| 5,697,981 A | 12/1997 | Ison et al. | |
| 5,783,248 A | 7/1998 | Lin et al. | |
| 5,814,681 A | 9/1998 | Hino et al. | |
| 5,874,109 A | 2/1999 | Ducheyne et al. | |
| 5,875,799 A | 3/1999 | Petrus | |
| 5,891,233 A | 4/1999 | Salonen et al. | |
| 5,900,254 A | 5/1999 | Constantz | |
| 5,914,356 A | 6/1999 | Erbe | |
| 5,952,010 A | 9/1999 | Constantz | |
| 5,954,867 A | 9/1999 | Chow et al. | |
| 5,962,028 A | 10/1999 | Constantz | |
| 5,968,253 A | * 10/1999 | Poser et al. | 106/691 |
| 5,976,234 A | 11/1999 | Chow et al. | |
| 5,997,624 A | 12/1999 | Chow et al. | |
| 6,000,341 A | 12/1999 | Tung | |
| 6,005,162 A | 12/1999 | Constantz | |
| 6,027,742 A | 2/2000 | Lee et al. | |
| 6,139,578 A | 10/2000 | Lee et al. | |
| 6,201,039 B1 | 3/2001 | Brown et al. | |
| 6,312,468 B1 | 11/2001 | Best et al. | |
| 6,323,146 B1 | 11/2001 | Pugh et al. | |
| 6,375,935 B1 | * 4/2002 | Constantz | 424/57 |
| 6,379,453 B1 | 4/2002 | Lin et al. | |
| 6,398,859 B1 | 6/2002 | Dickens et al. | |
| 6,451,059 B1 | 9/2002 | Janas et al. | |
| 6,458,423 B1 | 10/2002 | Goodson | |
| 6,461,632 B1 | 10/2002 | Gogolewski | |
| 6,518,212 B1 | 2/2003 | Wagh et al. | |

OTHER PUBLICATIONS

E. Fernandez Production and Characterization of new calcium phosphate none cements in the $CaHPO_4$–a–$Ca_3(PO_4)_2$ System:pH, workability and setting time.

Lacout et al. "Methods for Preparing A Calcium Phosphate Pasty Material For Injection" Pub. No. 2003/0021824A1, Pub Date: Jan. 30, 2003.

Lee et al. "Method of Preparing A Poorly Crystalline Calcium Phosphate and Methods of Its Use" Pub. No. 2003/0049329A1, Pub. Date: Mar. 13, 2003.

* cited by examiner

Primary Examiner—Thurman K. Page
Assistant Examiner—Charesse Evans
(74) Attorney, Agent, or Firm—Bret E. Field; Bozicevic, Field & Francis LLP

(57) ABSTRACT

Methods are provide for producing flowable compositions, e.g. pastes, that set into calcium phosphate products. In the subject methods, dry reactants that include a calcium source and a phosphate source are combined with a solution of a soluble silicate, e.g. sodium silicate, and the combined liquids and solids are mixed to produce the flowable composition. Also provided are the compositions themselves as well as kits for preparing the same. The subject methods and compositions produced thereby find use in a variety of applications, including the repair of hard tissue defects, e.g. bone defects.

21 Claims, No Drawings

CALCIUM PHOSPHATE CEMENTS PREPARED FROM SILICATE SOLUTIONS

CROSS-REFERENCE TO RELATED APPLICATIONS

This application is a continuation-in-part of application Ser. No. 09/561,324 filed Apr. 28, 2000 now U.S. Pat. No. 6,375,935; the disclosure of which is herein incorporated by reference.

INTRODUCTION

1. Field of the Invention

The field of this invention is calcium phosphate cements.

2. Background

Calcium phosphate cements which are prepared by combining a dry component(s) and a liquid to form a flowable paste like material that is subsequently capable of setting into a solid calcium phosphate product hold great promise for use as structural materials in the orthopedic and dental fields. For example, it is desirable to be able to inject a flowable material into a cancellous bone void and have the material set into a solid calcium phosphate mineral product that is capable of withstanding physiological loads. Materials that set into solid calcium phosphate mineral products are of particular interest as such products can closely resemble the mineral phase of natural bone and are susceptible to remodeling, making such products extremely attractive for use in orthopedics and related fields.

While a large number of different calcium phosphate cement formulations have been developed, there is a continued need for the development of yet more advanced formulations. Of particular interest is the development of formulations that set in a clinically relevant period of time into products that have sufficient strength to serve as cancellous and cortical bone substitutes and are capable of being replaced over time with natural bone.

Relevant Literature

Calcium phosphate compositions relevant to this invention include, but are not limited to those described in: "Production and Characterization of New Calcium Phosphate Cements in the CAHPO4-alpha-CA3(PO4)2 System: pH, Workability and Setting Times"; J. Materials Science: Materials in Medicine, v. 10 (1999) pp.223–230. Representative Patents describing calcium phosphate cements include: U.S. Pat. Nos. 6,139,578; 6,027,742; 6,005,162; 5,997,624; 5,976,234; 5,968,253; 5,962,028; 5,954,867; 5,900,254; 5,697,981; 5,695,729; 5,679,294; 5,580,623; 5,545,254; 5,525,148; 5,281,265; 4,990,163; 4,497,075; and 4,429,691. Sodium hexafluorosilicate is described in U.S. Pat. Nos.: 4,161,511 and 4,160,012.

SUMMARY OF THE INVENTION

Methods are provided for producing flowable compositions, e.g. injectable pastes, that set into calcium phosphate products. In the subject methods, dry reactants that include a calcium source and a phosphate source are combined with a solution of a soluble silicate, e.g. sodium silicate, and the combined liquids and solids are mixed to produce the flowable composition. Also provided are the compositions themselves as well as kits for preparing the same. The subject methods and compositions produced thereby find use in a variety of applications, including the repair of hard tissue defects, e.g. bone defects.

DESCRIPTION OF THE SPECIFIC EMBODIMENTS

Methods are provided for producing flowable compositions, e.g. injectable pastes, that set into calcium phosphate products. In the subject methods, dry reactants that include a calcium source and a phosphate source are combined with a solution of a soluble silicate, e.g. sodium silicate, and the combined liquids and solids are mixed to produce the flowable composition. Also provided are the compositions themselves as well as kits for preparing the same. The subject methods and compositions produced thereby find use in a variety of applications, including the repair of hard tissue defects, e.g. bone defects. In further describing the subject invention, the subject methods will be described first, followed by a description of the compositions produced thereby, kits for use in preparing the same and methods for using the subject compositions in methods of hard tissue, e.g. bone repair.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

It must be noted that, as used in this specification and the appended claims, the singular forms "a," "an" and "the" include plural reference unless the context clearly dictates otherwise. Unless defined otherwise all technical and scientific terms used herein have the same meaning as commonly understood to one of ordinary skill in the art to which this invention belongs.

Where a range of values is provided, it is understood that each intervening value, to the tenth of the unit of the lower limit, unless the context clearly dictates otherwise, between the upper and lower limit of that range and any other stated or intervening value in that stated range, is encompassed within the invention. The upper and lower limits of these smaller ranges may independently be included in the smaller ranges, and such embodiments are also encompassed within the invention, subject to any specifically excluded limit in the stated range. Where the stated range includes one or both of the limits, ranges excluding either or both of those included limits are also included in the invention.

All publications mentioned herein are incorporated herein by reference for the purpose of describing and disclosing components that are described in the publications that might be used in connection with the presently described invention.

METHODS

In the subject methods, dry reactants that include a calcium source and a phosphate source are combined with a solution of a soluble silicate under conditions sufficient to produce a flowable composition that sets into a calcium phosphate containing product, even when immersed.

A feature of the subject methods is that a solution of a soluble silicate is employed. By solution of a soluble silicate is meant an aqueous solution in which a silicate compound is dissolved and/or suspended. The silicate compound may be any compound that is physiologically compatible and is soluble in water. By soluble in water is meant a concentration of at least about 1%, usually at least about 2% and more usually at least about 5%, where the concentration of the silicate employed typically ranges from about 0 to 20%, usually from about 5 to 15% and more usually from about 5 to 10%. Representative silicates of interest include, but are not limited to: sodium silicates, potassium silicates, borosilicates, magnesium silicates, aluminum silicates, zirconium silicates, potassium aluminum silicates, magnesium aluminum silicates, sodium aluminum silicates, sodium methylsilicates, potassium methylsilicates, sodium butylsilicates, sodium propylsilicates, lithium propylsilicates, triethanol ammonium silicates, tetraethanolamine silicates, zinc hexafluorosilicate, ammonium hexafluorosilicate, cobalt hexafluorosilicate, iron hexafluorosilicate, potassium hexafluorosilicate, nickel hexafluorosilicate, barium hexafluorosilicate, hydroxyammonium hexafluorosilicate, sodium hexafluorosilicate and calcium fluorosilicate. The preparation of sodium hexafluorosilicate is described in U.S. Pat. Nos. 4,161,511 and 4,160,012; the disclosures of which are herein incorporated by reference. Of particular interest in many embodiments are solutions of sodium silicate, where the manufacture of dry sodium silicate (Na2SiO3, Na6Si2O7 and Na2Si3O7) is described in Faith, Keyes & Clark's INDUSTRIAL CHEMICALS (1975) pp 755–761.

In the subject methods, the above described soluble silicate solutions are combined with dry reactants that include a calcium source and a phosphate source under conditions sufficient to produce a flowable composition. The dry reactants that are combined with the solution are typically particulate compositions, e.g. powders, where the particle size of the components of the particulate compositions typically ranges from about 1 to 1000 microns, usually from about 1 to 200 um and more usually from about 1 to 40 microns.

As mentioned above, the dry reactants include a calcium source and a phosphate source. The calcium source and phosphate source may be present as a single compound or present as two or more compounds. As such, a single calcium phosphate present in the dry reactants may be the calcium source and the phosphate source. Alternatively, two or more compounds may be present in the dry reactants, where the compounds may be compounds that include calcium, phosphate or calcium and phosphate. Calcium phosphate sources of interest that may be present in the dry reactants include: MCPM (monocalcium phosphate monohydrate or $Ca(H_2PO_4)_2 \cdot H_2O$); DCPD (dicalcium phosphate dihydrate, brushite or $CaHPO_4 \cdot 2H_2O$), ACP (amorphous calcium phosphate or $Ca_3(PO_4)_2H_2O$), DCP (dicalcium phosphate, monetite or $CaHPO_4$), tricalcium phosphate, including both α- and β- $(Ca_3(PO_4)_2$, tetracalcium phosphate $(Ca_4(PO_4)_2O$, etc. Calcium sources of interest include: calcium carbonate ($CaCO_3$), calcium oxide (CaO), calcium hydroxide $(Ca(OH)2$ and the like. Phosphate sources of interest include: Phosphoric acid ($H3PO4$), all soluble phosphates, and the like.

The ratios or relative amounts of each of the disparate calcium and/or phosphate compounds in the dry reactant mixture is one that provides for the desired calcium phosphate product upon combination with the soluble silicate and subsequent setting. In many embodiments, the overall ratio (i.e. of all of the disparate calcium and/or phosphate compounds in the dry reactants) of calcium to phosphate in the dry reactants ranges from about 4:1 to 0.5:1, usually from about 2:1 to 1:1 and more usually from about 1.33:1 to 1.9:1. A variety of calcium phosphate cement compositions are known to those of skill in the art, and such cements may be readily modified into cements of the subject invention by substituting a silicate containing solution for the setting solution of those cements. Cement compositions known to those of skill in the art and of interest include, but are not limited to, those described in U.S. Pat. Nos.: 6,027,742; 6,005,162; 5,997,624; 5,976,234; 5,968,253; 5,962,028; 5,954,867; 5,900,254; 5,697,981; 5,695,729; 5,679,294; 5,580,623; 5,545,254; 5,525,148; 5,281,265; 4,990,163; 4,497,075; and 4,429,691; the disclosures of which are herein incorporated by reference.

One or both of the above liquid and dry reactant components may include an active agent that modulates the properties of the product into which the flowable composition prepared by the subject method sets. Such additional ingredients or agents include: organic polymers, e.g. proteins, including bone associated proteins which impart a number of properties, such as enhancing resorption, angiogenesis, cell entry and proliferation, mineralization, bone formation, growth of osteoclasts and/or osteoblasts, and the like, where specific proteins of interest include osteonectin, bone sialoproteins (Bsp), α-2HS-glycoproteins, bone Gla-protein (Bgp), matrix Gla-protein, bone phosphoglycoprotein, bone phosphoprotein, bone proteoglycan, protolipids, bone morphogenic protein, cartilage induction factor, platelet derived growth factor, skeletal growth factor, and the like; particulate extenders; inorganic water soluble salts, e.g. NaCl, calcium sulfate; sugars, e.g. sucrose, fructose and glucose; pharmaceutically active agents, e.g. antibiotics; and the like.

In practicing the subject methods, suitable amounts of the dry reactants and the silicate solution are combined to produce a flowable composition. In other words, the ratio of the dry reactants to silicate solution (i.e. the liquid to solids ratio) is selected to provide for a flowable composition. In many embodiments, the liquid to solids ratio is chosen to provide for a flowable composition that has a viscosity ranging from that of milk to that of modeling clay. As such, the liquids to solids ratio employed in the subject methods typically ranges from about 0.2 to 1.0, usually from about 0.3 to 0.6. Of particular interest in many embodiments are methods that produce a paste composition, where the liquid to solids ratio employed in such methods typically ranges form about 0.25 to 0.5, usually from about 0.3 to 0.45. The use of sodium silicate as the liquid allows a lower liquids to solids ratio to be employed which results in a less porous and stronger final hardened mass.

As mentioned above, the requisite amounts of dry reactants and silicate solution are combined under conditions sufficient to produce the flowable product composition. As such, the dry and liquid components are typically combined under agitation or mixing conditions, such that a homogenous composition is produced from the dry and liquid components. Mixing may be accomplished using any convenient means, including manual mixing as described in U.S. Pat. No. 6,005,162 and automated mixing as described in WO 98/28068, the disclosures of which are herein incorporated by reference. Also of interest is the device disclosed in U.S. Pat. No. 5,980,482, the disclosure of which is herein incorporated by reference.

Because the silicate solution enhances the speed and mixablility of the components, a simple cylindrical tube may be used both as a storage and packaging device and a mixing and delivery device. The plastic tube is separated into at least two, and usually two sections, compartments or portions. One section or portion contains the silicate solution, as described above, and another section, compartment or portion contains the powder component, as described above. The two compartments are separated from each other by an easily removable barrier which can be readily removed during preparation of the packaged cement. Any convenient removable barrier may be present in the device, where a representative barrier means of interest is a dialysis bag clips or analogous means. Another representative barrier means of interest is a frangible barrier, as described in WO 98/28068 and U.S. Pat. No. 5,362,654; the disclosures of which are herein incorporated by reference. When one is ready to mix, the clip or other barrier means between the to areas (liquid and powder) is removed (e.g. unclipped), and the contents are simply kneaded together by hand. The above steps may be performed through a second outer covering for sterility—i.e. the above described package elements may be present in a second outer covering for sterility. The outer coving may then be removed and the mixed contents from the tube may be delivered from one end of the storage/mixing tube using a peristaltic action. This mixing device is exceedingly simple to use and inexpensive to supply, with no additional components necessary;—the entire mixing device is disposable. This device provides advantages over that described in U.S. Pat. No. 5,980,482.

The temperature of the environment in which combination or mixing of the dry and liquid components takes place is sufficient to provide for a product that has desired setting and strength characteristics, and typically ranges from about 0 to 50 degrees C., usually from about 20 to 30 degrees C. Mixing takes place for a period of time sufficient for the flowable composition to be produced, and generally takes place for a period of time ranging from about 15 to 100 seconds, usually from about 15 to 50 seconds and more usually from about 15 to 30 second. By employing sodium silicate mixing times are shorter than with other liquids which have been used and the paste has a "slippery" feel.

The above described protocols result in a flowable composition that is capable of setting into a calcium phosphate mineral product, as described in greater detail below.

FLOWABLE COMPOSITIONS

The flowable compositions produced by the above described methods are ones that set into a biologically compatible, and often resorbable and/or remodelable, product, where the product is characterized by including calcium phosphate molecules not present in the initial reactants, i.e., that are the product of a chemical reaction among the initial reactants. The term flowable is meant to include paste like compositions, as well as more liquid compositions. As such, the viscosity time of the subject flowable compositions, defined as time periods under which the mixed composition injects through a standard Luer-lok fitting after mixing, typically ranges up to 10 minutes, usually up to 7 minutes and more usually up to 4 minutes. Of particular interest in many embodiments are paste compositions that have a injectable viscosity ranging up to 5 minutes, usually from about up to 4 minutes. Pastes that stay paste-like for longer period may be displaced by bleeding bone once inplanted into the body, which create a blood interface between the cement and the bone prior to the cement hardening.

The compositions produced by the subject invention set into calcium phosphate mineral containing products. By calcium phosphate mineral containing product is meant a solid product that includes one or more, usually primarily one, calcium phosphate mineral. In many embodiments, the calcium phosphate mineral is one that is generally poorly crystalline, so as to be resorbable and, often, remodelable, over time when implanted into a physiologically site. The calcium to phosphate ratio in the product may vary depending on particular reactants and amounts thereof employed to product it, but typically ranges from about 2:1 to 1.33:1, usually from about 1.5:1 to 1.8:1 and more usually from about 1:6:1 to 1.7:1. Of particular interest in many embodiments are apatitic products, which apatitic products have a calcium to phosphate ratio ranging from about 1.33:1 to 2.0:1, including both hydroxyapatite and calcium deficient analogs thereof, including carbonate substituted hydroxyapatite (i.e. dahllite), etc. The subject paste-like composition is in many embodiments, preferably one that is capable of setting into a hydroxyapatitic product, and more preferably into a carbonated hydroxyapatite, i.e. dahllite, having a carbonate substitution of from 2 to 10%, usually 2 to 8% by weight of the final product.

The period of time required for the compositions to harden or "set" may vary. By set is meant: the Gilmore Needle Test (ASTM C266-89), modified with the cement submerged under 37 degree C. physiological saline. The set times of the subject cements may range from about 30 second to 30 minutes, and will usually range from about 2 to 15 minutes and more usually from about 4 to 12 minutes. In many embodiments, the flowable composition sets in a clinically relevant period of time. By clinically relevant period of time is meant that the paste-like composition sets in less than about 20 minutes, usually less than about 15 minutes and often in less than about 10 minutes, where the composition remains flowable for at least about 1 minute, usually at least about 2 minutes and, in many embodiments, for at least about 5 minutes following combination or mixture of the precursor liquid and dry cement components. The use of silicate solutions cause these cements to set faster than the same cements do when only water is employed; the rate of setting increase positively with increasing silicate concentrations.

The compressive strength of the product into which the flowable composition sets may vary significantly depending on the particular components employed to produce it. Of particular interest in many embodiments is a product that has a compressive strength sufficient for it to serve as at least a cancellous bone structural material. By cancellous bone structural material is meant a material that can be used as a cancellous bone substitute material as it is capable of withstanding the physiological compressive loads experienced by compressive bone under at least normal physiological conditions. As such, the subject flowable paste-like material is one that sets into a product having a compressive strength of at least about 20, usually at least about 40 and more usually at least about 50 MPa, as measured by the assay described in Morgan, EF et al . . . , 1997, Mechanical Properties of Carbonated Apatite Bone Mineral Substitute: Strength, Fracture and Fatigue Behavior. J. Materials Science: Materials in Medicine. V. 8, pp 559–570. where the compressive strength of the final apatitic product may be as high as 60 or higher. Inclusion of the silicate allows lower liquid to solids ratios to be employed which results in significantly higher compressive strengths. Compressive strengths can be obtained that range as high 100 to 200 MPa.

Preferably, the flowable paste like composition is capable of setting in a fluid environment, such as an in vivo environment at a bone repair site. As such, the flowable paste composition can set in a wet environment, e.g. one that is filled with blood and other physiological fluids. Therefore, the site to which the flowable composition is administered during use need not be maintained in a dry state.

In certain embodiments, the subject cement compositions may be seeded with any of a variety of cells. A "cell", according to the present invention, is any preparation of living tissue, including primary tissue explants and preparations thereof, isolated cells, cells lines (including transformed cells), and host cells. Preferably, autologous cells are employed, but xenogeneic, allogeneic, or syngeneic cells are also useful. As such, the cells can be obtained directly from a mammalian donor, e.g., a patient's own cells, from a culture of cells from a donor, or from established cell culture lines. The mammal can be a mouse, rat, rabbit, guinea pig, hamster, cow, pig, horse, goat, sheep, dog, cat, and the mammal can be a human. Cells of the same species and preferably of the same immunological profile can be obtained by biopsy, either from the patient or a close relative. Where the cells are not autologous, it may be desirable to administer immunosuppressive agents in order to minimize rejection. In preferred embodiments, such agents may be included within the seeded composition to ensure effective local concentrations of the agents and to minimize systemic effects of their administration. The cells employed may be primary cells, explants, or cell lines, and may be dividing or non-dividing cells. Cells may be expanded ex-vivo prior to introduction into the inventive cement compositions. Autologous cells are preferably expanded in this way if a sufficient number of viable cells cannot be harvested from the host.

Any preparation of living cells may be use to seed the cement composition of the present invention. For example, cultured cells or isolated individual cells may be used. Alternatively or additionally, pieces of tissue, including tissue that has some internal structure, may be used. The cells may be primary tissue explants and preparations thereof, cell lines (including transformed cells), or host cells.

Any available methods may be employed to harvest, maintain, expand, and prepare cells for use in the present invention. Useful references that describe such procedures include, for example, Freshney, Culture of Animal Cells: a Manual of Basic Technique, Alan R. Liss Inc., New York, N.Y., incorporated herein by reference.

The cement composition material of the invention is useful as a scaffold for production of hard or soft tissues. Tissue-producing or -degrading cells that may be incorporated into the material include, but are not limited to, chondrocytes, osteocytes, osteoblasts, osteoclasts, mesenchymal stem cells, other bone- or cartilage-producing cells or cell lines, fibroblasts, muscle cells, hepatocytes, parenchymal cells, cells of intestinal origin, nerve cells, and skin cells.

Methods of isolating and culturing such tissue-producing or -degrading cells, and/or their precursors, are known in the art (see, for example, Vacanti et al., U.S. Pat. No. 5,041,138; Elgendy et al., Biomater. 14:263, 1993; Laurencin et al., J. Biomed. Res. 27:963, 1993; Freed et al., J. Cell. Biochem. 51:257, 1993; Atala et al., J. Urol. 150:745, 1993; Ishaug et al., J. Biomed. Mater. Res. 28:1445, 1994; Chu et al., J. Biomed. Mater. Res. 29:1147, 1995; Thomson et al., J. Biomater. Sci. Polymer Edn. 7:23, 1995, each of which is incorporated by reference).

For example, mesenchymal stem cells, which can differentiate into a variety of mesenchymal or connective tissues (including, for example, adipose, osseous, cartilagenous, elastic, and fibrous connective tissues), can be isolated, purified, and replicated according to known techniques (see Caplan et al., U.S. Pat. No. 5,486,359; Caplan et al., U.S. Pat. No. 5,226,914; Dennis et al., Cell Transplantation 1:23, 1992, each of which is incorporated herein by reference). Such mesenchymal cells have been studied in association with tricalcium phosphate and hydroxyapatite carriers and have been found to be capable of successful differentiation from within such carriers (see Caplan et al., U.S. Pat. No. 5,197,985, incorporated herein by reference). Similar procedures are employed to direct mesenchymal cell differentiation within the cement material of the present invention.

Of course, the present invention is not limited to the use of tissue-producing cells. Certain preferred embodiments of the invention utilize such cells, primarily because the inventive material is so well suited to tissue-regeneration applications (particularly with those involving growth of bone and/or cartilage). Any cell may be seeded into the material of the invention. In some cases, it will be desirable to include other cells in addition with tissue-producing cells.

Any convenient cell source may be employed. For example, where the material is seeded with stem cells, e.g., adult stem cells, mesenchymal stem cells, any convenient stem cell source may be employed. Stem cell sources of interest include bone marrow, cord blood, etc., which source may be treated to enrich the target stem cell population of interest, e.g., fractionated, etc.

The cells that are seeded into the inventive cement composition may be genetically engineered, for example to produce a protein or other factor that it useful in the particular application. In preferred embodiments, cells may be engineered to produce molecules that impart resistance to host immune attack and rejection. The Fas-L and CR-1 genes are examples of useful such genes.

Generally, cells are introduced into the subject material of the present invention in vitro, although in vivo seeding approaches are employed in some circumstances. Cells are typically mixed with the cement composition prior to setting.

Any available method may be employed to introduce the cells into the cement composition material. For example, cells may be injected into the flowable cement composition (sometimes in combination with growth medium), or maybe introduced by other means such as pressure, vacuum, or osmosis. Alternatively (or additionally), cells may be layered on the flowable cement composition. In certain embodiments, it may be desirable to manually mix or knead the cells with the material paste. Cells may also be introduced into the hydrated precursor in vivo simply by placing the material in the body adjacent a source of desired cells. In some cases, it may be desirable to enhance such in vivo cell impregnation by including within the material an appropriate chemotactic factor, associative factor (i.e., a factor to which cells bind), or factor that induces differentiation of cells into the desired cell type.

As those of ordinary skill will readily appreciate, the number of cells to be introduced into the inventive material will vary based on the intended application of the seeded material and on the type of cell used. Where dividing autologous cells are being introduced by injection into the hydrated precursor, use of 20,000–1,000,000 cells per $cm^3$ are expected to result in cellular proliferation and extracellular matrix formation within the material. Where non-dividing cells are employed, larger numbers of cells will generally be required. In those cases where seeding is accomplished by host cell migration into the material in vivo, exposure of the material to fluids containing cells (e.g., bone-forming cells), or to tissue (e.g., bone) itself has proven to be effective to seed the material with cells without the need for inoculation with a specified number of cells. The use of cells as described above is further described in U.S. Pat. No. 6,139,578 and the references cited therein, the disclosures of which are herein incorporated by reference.

With respect to cell seeded cements, as described above, the subject invention is not limited to cements prepared from a silicate solution, as described above, but instead provides any structural cement seeded with cells. By structural cement is meant a cement composition that, upon setting, achieves a compressive strength of at least about 20, usually at least about 40 and more usually at least about 50 MPa, as measured by the assay described in Morgan, EF et al . . . , 1997, Mechanical Properties of Carbonated Apatite Bone Mineral Substitute: Strength, Fracture and Fatigue Behavior. J. Materials Science: Materials in Medicine. V. 8, pp 559–570, where the compressive strength of the final apatitic product may be as high as 60 or higher, e.g., as as high 100 to 200 MPa or higher. Cements other than the specific cements described herein that qualify as structural cements include, but are not limited to, those described in: U.S. Pat. Nos. 6,027,742; 6,005,162; 5,997,624; 5,976,234; 5,968,253; 5,962,028; 5,954,867; 5,900,254; 5,697,981; 5,695,729; 5,679,294; 5,580,623; 5,545,254; 5,525,148; 5,281,265; 4,990,163; 4,497,075; and 4,429,691; the disclosures of which are herein incorporated by reference.

Seeding a structural cement with plurlipotent cells according to the above description results in stress induced cell differentiation of the pluripotent cells, e.g., into bone forming cells, i.e., osteoblasts. As such, the subject invention provides methods of differentiating pluripotent cells into bone form cells via stress induction, wherein a sufficient amount of pluripotent cells are seeded in a structural cement as described above, which is subsequently allowed to set and, upon setting, results in stress induced differentiation of cells seeded therein as a result of mechanical forces applied to the set cement composition.

In the subject methods, it is important to employ a structural cement having a compressive strength that is comparable to cancellous bone, i.e., has a compressive strength of at least about 20 mPa. Such a feature is important because it is this feature that causes a stress induced differentiation of pluripotent cells present in the cement. As such, the term "structural cement" as used herein does not include cements that do not achieve a compressive strength of at least about 20 mPa, as such cements cannot provide the desired stress induced differentiation. Likewise, the term "structural cement" does not include a composition that sets into a structure which fractures in response to stress—i.e., the composition must remain as one homogeneous mass under applied physiological stresses and not be a composition that will fracture, as the latter type of composition gives rise to the formation of fibrous tissue, which is not a desirable outcome for the subject invention.

In addition, in certain embodiments the compositions include demineralized bone matrix, which may be obtained typically in lyophilized or gel form and is combined with the cement composition at some prior to implantation. A variety of demineralized bone matrixes are known to those of skill in the art and any convenient/suitable matrix composition may be employed.

APPLICATIONS

The subject methods and compositions produced thereby, as described above, find use in applications where it is desired to introduce a flowable material capable of setting up into a solid calcium phosphate product into a physiological site of interest, such as in dental, craniomaxillofacial and orthopedic applications. In orthopedic applications, the cement will generally be prepared, as described above, and introduced to a bone repair site, such as a bone site comprising cancellous and/or cortical bone. Orthopedic applications in which the cements prepared by the subject system find particular use include the treatment of fractures and/or implant augmentation, in mammalian hosts, particularly humans. In such fracture treatment methodologies, the fracture is first reduced. Following fracture reduction, a flowable structural material prepared by the subject system is introduced into the cancellous tissue in the fracture region using the delivery device described above. Specific dental, craniomaxillofacial and orthopedic indications in which the subject invention finds use include, but are not limited to, those described in U.S. Pat. No. 6,149,655, the disclosure of which is herein incorporated by reference. In addition to these particular applications described in this U.S. Patent, the subject cement compositions also find use in applications where a sternotomy has been performed. Specifically, the subject cements find use in the closure process of a sternotomy, where the bone fragments are rejoined and wired together, and any remaining cracks are filled with the subject cement. In yet other embodiments, the subject compositions find use in drug delivery, where they are capable of acting as long lasting drug depots following administration to a physiological site. See e.g. U.S. Pat. Nos. 5,904,718 and 5,968,253; the disclosures of which are herein incorporated by reference.

KITS

Also provided are kits comprising the subject cements, where the dry and liquid components may be present in separate containers in the kit, or some of the components may be combined into one container, such as a kit wherein the dry components are present in a first container and the liquid components are present in a second container, where the containers may or may not be present in a combined configuration, as described in U.S. Pat. No. 6,149,655, the disclosure of which is herein incorporated by reference. In addition to the cement compositions, the subject kits may further include a number of additional reagents, e.g., cells (as described above, where the composition is to be seeded), protein reagents (as described above), and the like.

Kits can also include device for aspirating marrow, e.g., needle and trocar, which finds use for harvesting marrow (i.e. a pluripotent cell source) from a patient. Such components find use in those embodiments where the kit is employed in a method where the structure cement is seeded with the patient's own marrow, such as that described in Example 4, below.

In addition to above mentioned components, the subject kits typically further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

The following examples are offered by way of illustration and not by way of limitation.

EXPERIMENTAL

Example 1

5 grams of Norian SRS combined powder (MCPM, Calcite, alpha-TCP; NSWO#455A) (available from Norian Corporation, Cupertino Calif.) was combined in a glass mortar and pestal with 4.0 grams of sodium silicate liquid (Fischer Scientific). The mixture hardened very rapidly, in less than one minute. There was no apparent or measurable heat evolved. Hardened pieces were immersed in distilled water. The pH of the wetted hard cement was approximately 10.

Example 2

A dilute sodium silicate solution was prepared by dissolving 2 ml of sodium silicate liquid (Fischer Scientific) in 24 ml of distilled water. The pH of this diluted solution was 11.5. 5 grams of Norian SRS combined powder (MCPM, Calcite, alpha-TCP; NSWO#455A) was combined in a glass mortar and pestal with 2.5 grams of the dilute sodium silicate solution. The mixture was ground in a glass mortar and pestal for two minutes, forming a very creamy paste almost instantly. No thermal evolution or odor was observed. At two minutes the paste was 'squeegied' out of the mortar and had a nice, very workable and injectable consistency. The paste was formed into two spheres and immersed in distilled water at room temperature. The spheres were hard to the touch at 10 minutes and it was difficult to make an impression on their surfaces. Distilled water was put in the mortar, exposed to the paste remaining in the mortar which was strongly adherent to the mortar wall and would not wash away with the jet of distilled water. The pH of the water coating the hardened paste was between 7 and 8, approximately 7.8. After immersion in distilled water for one day, one week and one month, the spheres remained intact and appeared to have compressive strength well in excess of 50 mPa.

Example 3

Another preferred base formulation is:

1.5 $CaHPO_4$ + 0.5 $CaCO_3$ + $Ca_3(PO_4)_2$ which is mixed with diluted sodium silicate solution to yield $Ca_5$-$^z/_2Na_z$ $(PO_4)_3$-$^2/_3x$-$^4/_3y(CO_3)x$ $(SiO_4)yOH$ + $Na^+$ + $HCO_3^-$ (excess)

Example 4

2 ccs of marrow are aspirated from an intermedullary access site, e.g., from an open fracture or percutaneously, from a patient. Cement prepared according to Example 2 is combined with harvested marrow by carefully folding the harvested marrow into the prepared paste cement composition without grinding, e.g., with a spatula. The resultant seeded mixture is then implanted into the bony defect site of the patient and allowed to set.

Example 5

Cement prepared according to Example 2 is combined with lyophilized demineralized bone matrix by carefully folding the matrix into the prepared paste cement composition without grinding, e.g., with a spatula. The resultant mixture is then implanted into the bony defect site of a patient and allowed to set.

It is evident from the above results and discussion that calcium phosphate cements employing silicate liquids may be mixed very quickly and easily without specialized mixing devices, set rapidly, and are able to obtain higher strengths due to the lower liquids to solids ratios employed. As such, the subject invention represents a significant contribution to the art.

All publications and patent applications mentioned in this specification are herein incorporated by reference to the same extent as if each individual publication or patent application was specifically and individually indicated to be incorporated by reference.

The invention now being fully described, it will be apparent to one of skill in the art that many changes and modifications can be made thereto without departing from the spirit and scope of the appended claims.

What is claimed is:

1. A method of producing a flowable composition that sets into a calcium phosphate containing product in an in vivo fluid environment said method comprising:

combining:
   (a) a silicate solution of a soluble silicate; and
   (b) dry reactants comprising a calcium source and a phosphate source, wherein said silicate solution and dry reactants are combined in a ratio sufficient to produce a flowable material that sets in an in vivo fluid environment into a calcium phosphate containing product having a compressive strength sufficient for said product to serve as a cancellous bone structure material.

2. The method according to claim 1, wherein said ratio ranges from about 0,2:1 to 0.7:1.

3. The method according to claim 2, wherein said flowable composition is a paste.

4. The method according to claim 1, wherein said silicate solution is a solution of a soluble silicate having a concentration ranging from about 1% to 15%.

5. The method according to claim 1, wherein said flowable composition sets into said calcium phosphate containing product in a period of time ranging from about 5 to 10 minutes.

6. The method according to claim 1, wherein said calcium phosphate containing product has a compressive strength ranging from about 25 to 100 MPa.

7. The method according to claim 1, wherein said method further comprises introducing cells into said flowable composition.

8. A method of producing a paste that sets into a calcium phosphate containing product in an in vivo fluid environment said method comprising:

(a) combining:
      (i) dry reactants comprising a calcium source and a phosphate source; and
      (ii) a solution of a soluble silicate having a concentration ranging from about 5% to 10%, wherein said dry reactants and said solution are combined in a ratio sufficient to provide for said paste; and
   (b) mixing said combined reactants and solution for a sufficient period of time to produce a paste capable of setting in an in vivo fluid environment into a calcium phosphate containing product having a compressive strength sufficient for said product to serve as a cancellous bone structure material.

9. The method according to claim 8, wherein said ratio ranges from about 0.3 to 0.5.

10. The method according to claim 8, wherein said paste sets in a period of time ranging from about 4 to 10 minutes into a calcium phosphate containing product having a compressive strength ranging from about 40 to 70 MPa.

11. The method according to claim 8, wherein said soluble silicate is sodium silicate.

12. The method according to claim 8, wherein said method further comprises introducing cells into said flowable composition.

13. A flowable composition that sets into a calcium phosphate containing product, wherein said composition is produced by the method comprising:

combining dry reactants comprising a source of calcium and phosphate with a solution of a soluble silicate; and
   mixing said combined dry reactants and solution for a period of time sufficient to produce said flowable product, wherein said flowable product sets in an in vivo fluid environment into a calcium phosphate containing product that has a compressive strength sufficient for said product to serve as a cancellous bone structural material.

14. The composition according to claim 13, wherein said composition is a paste.

15. The composition according to claim 13, wherein said calcium phosphate containing product is an apatitic product.

16. The composition according to claim 13, wherein said composition sets in period of time ranging from about 4 to 12 minutes.

17. The composition according to claim 13, wherein said calcium phosphate containing product has a compressive strength ranging from about 25 to 100.

18. The composition according to claim 13, wherein said composition further comprises cells.

19. A method of repairing a hard tissue defect, said method comprising:

applying to the site of said defect a flowable composition that sets into a calcium phosphate containing product, wherein said composition is produced by the method comprising:
(a) combining dry reactants comprising a source of calcium and phosphate with a solution of a soluble silicate; and
(b) mixing said combined dry reactants and solution for a period of time sufficient to produce said flowable product, wherein said flowable product sets into a calcium phosphate containing product that has a compressive strength sufficient for said product to serve as a cancellous bone structural material.

20. The method according to claim 19, wherein said composition is a paste.

21. The method according to claim 19, wherein said method further comprises introducing cells into said flowable composition.

* * * * *